(12) United States Patent
Meade et al.

(10) Patent No.: US 10,730,122 B2
(45) Date of Patent: Aug. 4, 2020

(54) OSSEOUS-SANDING ACCESSORY SYSTEM

(71) Applicant: Allosource, Centennial, CO (US)

(72) Inventors: Denis M. Meade, Littleton, CO (US); Shane Graham, Parker, CO (US)

(73) Assignee: ALLOSOURCE, Centennial, CO (US)

( * ) Notice: Subject to any disclaimer, the term of this patent is extended or adjusted under 35 U.S.C. 154(b) by 321 days.

(21) Appl. No.: 15/838,879

(22) Filed: Dec. 12, 2017

(65) Prior Publication Data

US 2018/0272446 A1 Sep. 27, 2018

Related U.S. Application Data

(60) Provisional application No. 62/475,549, filed on Mar. 23, 2017.

(51) Int. Cl.

| | |
|---|---|
| *B24B 45/00* | (2006.01) |
| *B23D 45/00* | (2006.01) |
| *B24B 27/06* | (2006.01) |
| *B24B 23/02* | (2006.01) |
| *B24B 19/00* | (2006.01) |
| *B23D 55/00* | (2006.01) |
| *A61F 2/46* | (2006.01) |
| *A61B 17/14* | (2006.01) |
| *B23D 45/06* | (2006.01) |

(52) U.S. Cl.
CPC ........... *B23D 45/003* (2013.01); *B23D 55/00* (2013.01); *B24B 19/00* (2013.01); *B24B 23/02* (2013.01); *B24B 27/0666* (2013.01); *B24B 45/00* (2013.01); *A61B 17/147* (2016.11); *A61B 17/149* (2016.11); *A61F 2002/4645* (2013.01); *B23D 45/06* (2013.01)

(58) Field of Classification Search
CPC ...... B23D 45/003; B23D 55/00; B23D 45/06; B24B 19/00; B24B 23/02; B24B 27/0666; B24B 45/003; B24B 45/006
USPC ....... 451/259, 420, 421, 461; 83/174, 174.1; 76/25.1
See application file for complete search history.

(56) References Cited

U.S. PATENT DOCUMENTS

| | | | |
|---|---|---|---|
| 667,960 A | * 2/1901 | Taber | ...... B24B 27/02 451/361 |
| 860,530 A | * 7/1907 | Cormany | ...... B26D 7/12 83/174 |

(Continued)

*Primary Examiner* — George B Nguyen
(74) *Attorney, Agent, or Firm* — James A. Sheridan; Sheridan Law, LLC

(57) ABSTRACT

There are disclosed systems and methods for safely and effectively removing the articular cartilage and cortical bone layers from an articular surface of a human cadaveric femoral head. One embodiment includes an osseous-sanding accessory system installed upon a conventional band saw having a motor and a cabinet that houses a pulley coupled with a primary drive shaft rotated by the motor. The accessory system may include a threaded drive shaft coupled with the primary drive shaft, a grinding disk having an abrasive surface and affixed about a distal end of the threaded drive shaft, and a removable accessory table mounted to the band saw below the grinding disk. When the motor rotates the primary drive shaft, and thus the threaded drive shaft, the grinding disk rotates relative to the accessory table and abrades osseous tissues introduced to the abrasive surface of the grinding disk. Other embodiments are also disclosed.

20 Claims, 7 Drawing Sheets

(56) References Cited

U.S. PATENT DOCUMENTS

| | | | | |
|---|---|---|---|---|
| 1,728,441 | A * | 9/1929 | Owens | B24B 19/00 |
| | | | | 451/242 |
| 2,079,076 | A * | 5/1937 | Kranich | B24B 53/14 |
| | | | | 451/439 |
| 2,724,932 | A * | 11/1955 | Wagner | B24B 19/00 |
| | | | | 451/276 |
| 3,803,771 | A * | 4/1974 | Bunn | B24B 19/00 |
| | | | | 451/359 |
| 4,661,009 | A * | 4/1987 | Tripp | B24B 45/006 |
| | | | | 279/157 |
| 4,729,193 | A * | 3/1988 | Gant | B24B 45/006 |
| | | | | 409/231 |
| 6,902,341 | B1 * | 6/2005 | Rauschert | F16C 11/0623 |
| | | | | 403/301 |
| 8,696,411 | B1 * | 4/2014 | Orlando | B24B 41/002 |
| | | | | 451/241 |
| 2002/0078796 | A1 * | 6/2002 | Brown | B23D 63/001 |
| | | | | 76/37 |

* cited by examiner

OSSEOUS-SANDING ACCESSORY SYSTEM

REFERENCE TO PENDING PRIOR PATENT APPLICATION

This application claims the benefit under 35 U.S.C. 119 (e) of U.S. Provisional Patent Application No. 62/475,549, filed Mar. 23, 2017 by Denis M. Meade and Shane Graham for "OSSEOUS-SANDING ACCESSORY SYSTEM," which patent application is hereby incorporated herein by reference.

BACKGROUND

An allograft includes bone, tendon, skin, or other types of tissue that is transplanted from one person to another. Allografts are used in a variety of medical treatments, such as knee replacements, bone grafts, spinal fusions, eye surgery, and skin grafts for the severely burned. Allografts come from voluntarily donated human tissue obtained from cadaveric donor-derived, living-related, or living-unrelated donors and can help patients regain mobility, restore function, enjoy a better quality of life, and even save lives in the case of cardiovascular tissue or skin.

Processing operations for osseous-based allografts often require the removal of articular cartilage from donated human cadaveric femoral heads. Operations also often involve the removal of outer layers of harder cortical bone to expose the more delicate cancellous bone required for an osseous-tissue donation beneath.

Currently, the removal of superficial cartilage and cortical bone layers from the articular surface of a cadaveric human femoral head occurs via one of three methods. The first method involves manually exposing the articular surface of the femoral head to a rotating, half-spherical steel drill bit having sharp cutting surfaces embedded within the sphere's interior dome. The bit also features a sharp, serrated edge that rims the circular, outside edge of the bit. The configuration of the rotating bit, when manually introduced to the articular surface, serves to abrade or strip the cartilage and outer bone layers from the femoral head. The second method involves a manual process whereby a technician repeatedly passes a sharp-edged gouge over the articular surface of the femoral head to remove the cartilage/bone layers in thin strips. The third and primary method of processing the articular surface involves introducing the femoral head into the sharp edge of a band-saw blade to remove the articular cartilage and cortical bone layers, again in thin strips.

Each of the current processing methods for preparing donated human cadaveric femoral heads presents significant drawbacks in the form of inherent risks to the operating technician and to the osseous tissue being processed. Existing hand tools used to prepare and process osseous-based allografts are not designed to safely process the non-uniform, asymmetrical contour of human femoral heads. For example, the drill bit method carries a risk of vibration-related injuries to the operator, while the gouge method carries risks of musculoskeletal injury due to the repetitive hand, wrist, shoulder, and arm motions required during processing. The band saw method carries traumatic laceration risks to the operator's hands and/or fingers, which are placed in the path of the band-saw blade. Without highly skilled technicians, all of the current methods present a risk of damage to the femoral head's underlying cancellous tissue. Moreover, all of the current methods are time consuming and inefficient, regardless of technician skill and/or experience level.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides an osseous-sanding accessory system for removable installation upon a commercial band saw having a motor operably coupled with a primary drive shaft, the primary drive shaft coupled with a blade pulley housed within a cabinet. The accessory system may include (1) a threaded drive shaft having a first end operably coupled with the motor via the primary drive shaft and a second end that extends outward from the cabinet; (2) a grinding disk having an abrasive surface, a center aperture, and a lower portion disposed below the center aperture, the center aperture of the grinding disk affixed about the second end of the threaded drive shaft; and (3) an accessory table having an upper platform forming a slot therein, the accessory table removably mounted to the cabinet such that the lower portion of the grinding disk extends into the slot, wherein when the motor of the band saw rotates the primary drive shaft, the threaded drive shaft rotates the grinding disk relative to the accessory table such that the abrasive surface abrades osseous tissues introduced to the abrasive surface of the grinding disk.

Another embodiment provides an accessory assembly for adapting a band saw for use in osseous-based sanding operations. The accessory assembly may include (1) a threaded drive shaft having a first end positioned adjacent a primary drive shaft of the band saw and a second end extending outward from a cabinet of the band saw; (2) a grinding disk coupled to the second end of the threaded drive shaft; and (3) a power coupling indirectly connecting a motor of the band saw with the first end of the threaded drive shaft, the power coupling comprising: (a) a first adaptor threadably coupled to the primary drive shaft of the band saw; (b) a second adaptor threadably coupled to the first end of the threaded drive shaft; and (c) a locking pin engaged with the first and the second adapters to mate the first and the second adapters with one another.

Yet another embodiment provides a method of removing articular cartilage and cortical bone layers from an articular surface of a human cadaveric femur bone using a band saw. The method may include (1) accessing a primary drive shaft of the band saw; (2) coupling a threaded drive shaft to the primary drive shaft of the band saw via a power coupling, the threaded drive shaft having a first end located at the primary drive shaft and a second end extending outward from a cabinet of the band saw; (3) affixing a grinding disk to the second end of the threaded drive shaft, the grinding disk having an abrasive surface; (4) removably attaching an accessory table to the cabinet of the band saw directly below the grinding disk, the accessory table having a number of adjustable legs that support a platform; (5) actuating a motor of the band saw such that the grinding disk rotates relative to the accessory table; (6) disposing the human cadaveric femur bone upon the platform of the accessory table; and (7) introducing the articular surface of the human cadaveric femur bone to the abrasive surface of the grinding disk to remove the articular cartilage and the cortical bone layers from the articular surface.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Various embodiments of the systems and methods described herein relate to the safe, efficient, and effective processing of osseous-based allografts using an osseous-sanding accessory system for installation upon a conventional band saw. As discussed above in the Background section, existing methods for removing articular cartilage and/or cortical bone layers from donated human cadaveric femoral heads include, for example, introducing to the articular surface to a rotating drill bit, a steel gouge, and/or a conventional band saw blade. These methods are not designed with an eye toward the safe manipulation of human femoral heads and present several utility and safety challenges, including the risk of vibration, repetitive-motion, musculoskeletal, and/or laceration injuries, as well as the risk of damage to the delicate cancellous tissue that is located beneath the articular cartilage and the cortical bone layers of the articular surface of the femoral head and that is needed for further allograft processing and ultimately surgical implantation.

Embodiments of the osseous-sanding accessory system disclosed herein are designed to address the particular challenges presented in the osseous-based allograft industry, with improved functionality that allows the operator or technician to efficiently remove superficial articular cartilage and cortical bone layers to expose the cancellous tissue beneath without causing damage to the cancellous tissue and without a lengthy, tedious, and repetitive process that risks operator injury.

Figure 1:
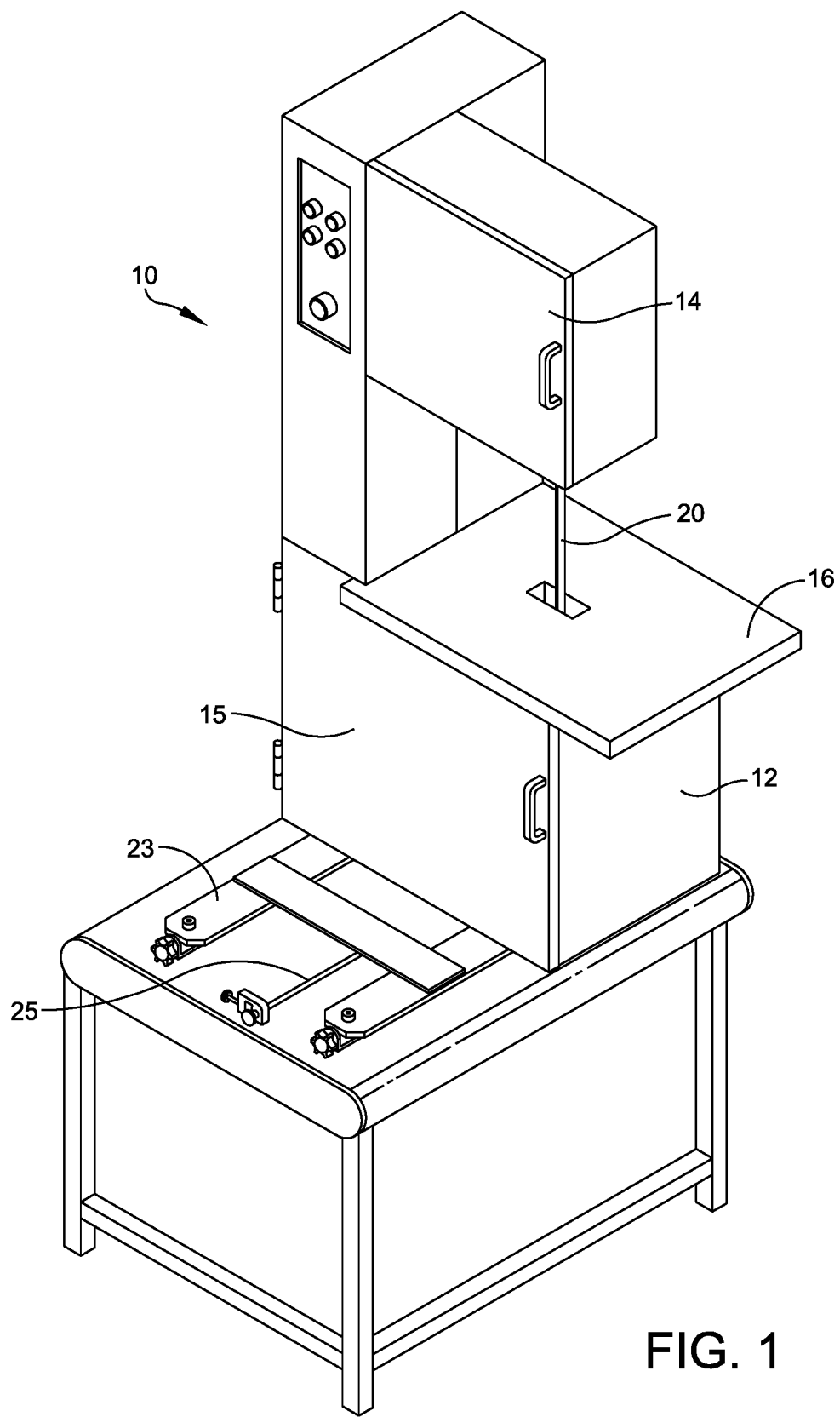
FIG. 1 illustrates a representative schematic of an embodiment of a conventional band saw commonly used in clean room environments.
Figure 2:
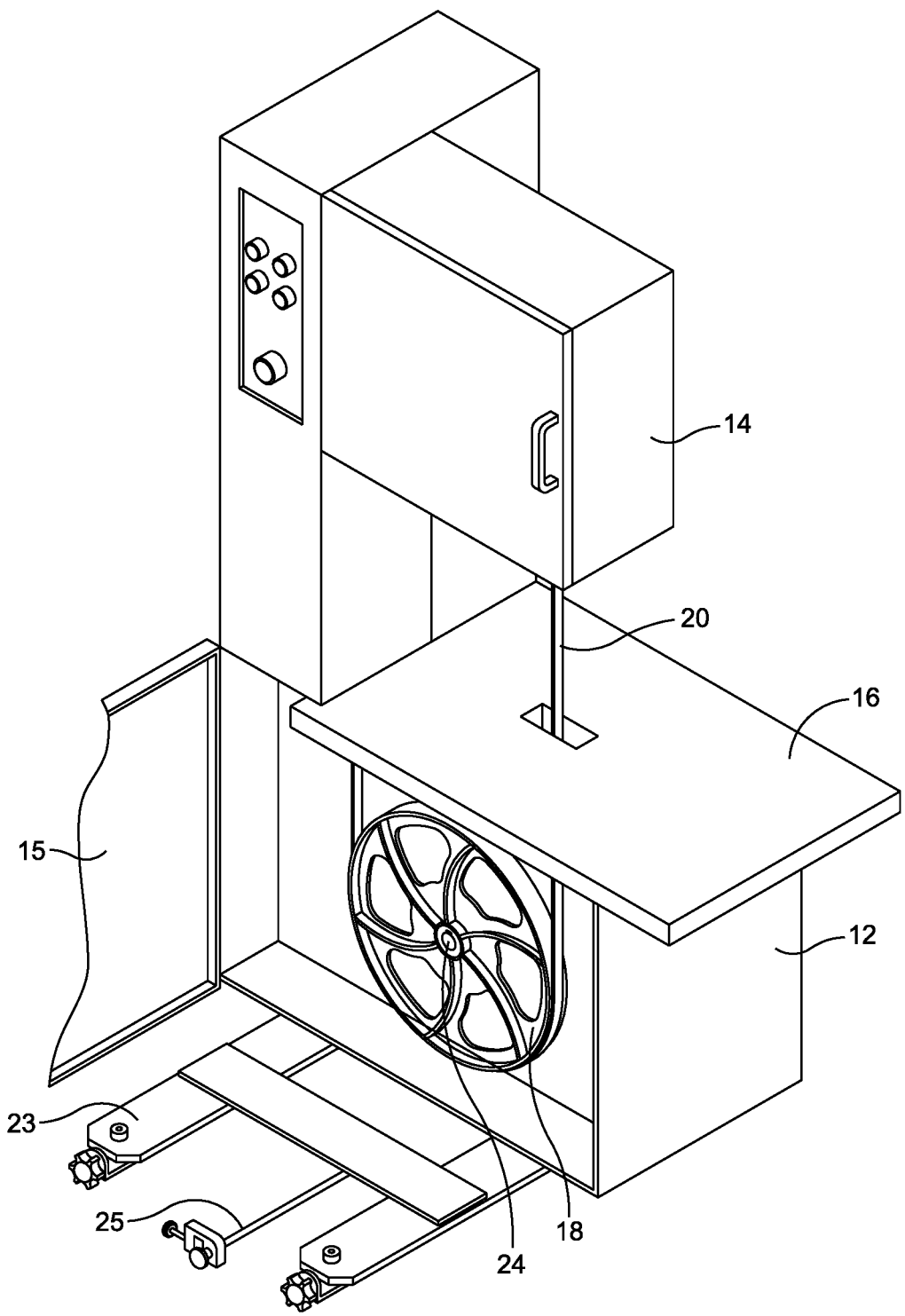
FIG. 2 illustrates a perspective view of the conventional band saw of FIG. 1, with an open lower cabinet and an exposed blade pulley.

FIGS. 1-2 illustrate perspective schematic representations of a conventional band saw 10 of the type that is suitable for a clean-room environment and that is commercially available through a number of brands and/or sales outlets. Band saws vary in configuration, though they generally include first and second cabinets 12, 14 having a band-saw table 16 disposed therebetween. As detailed in FIG. 2, each of the cabinets 12, 14 may include an access door 15 and may house a respective blade pulley 18. A conventional band-saw blade 20 may be stretched between the pulleys 18 of the first and the second cabinets 12, 14 such that the blade 20 is disposed about an outer perimeter of each of the pulleys 18. At least one of the pulleys 18 may be operably coupled with a motor 22 (FIG. 3) via a primary drive shaft 24. During conventional operation, the motor 22 may be switched on to rotate the primary drive shaft 24, which, in turn, rotates the associated pulley 18 and causes the band saw blade 20 to revolve about the spinning pulleys 18 for the purpose of performing cutting operations at the band-saw table 16.

Figure 3A:
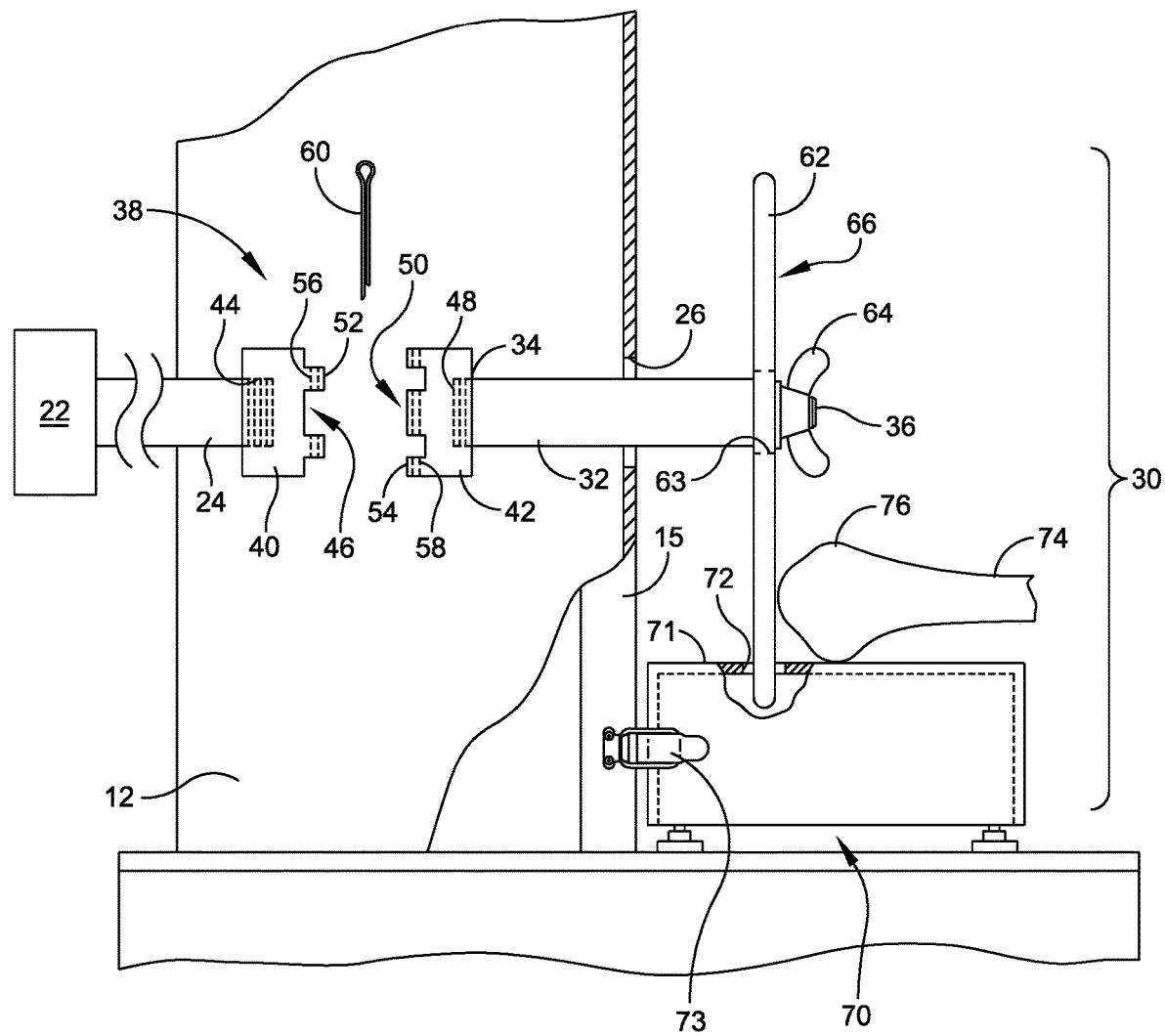
FIGS. 3A-3B illustrate side-partial views of the band saw of FIG. 1, with one embodiment of an osseous-sanding accessory system in respective pre-installed and installed configurations upon the conventional band saw.
Figure 3B:
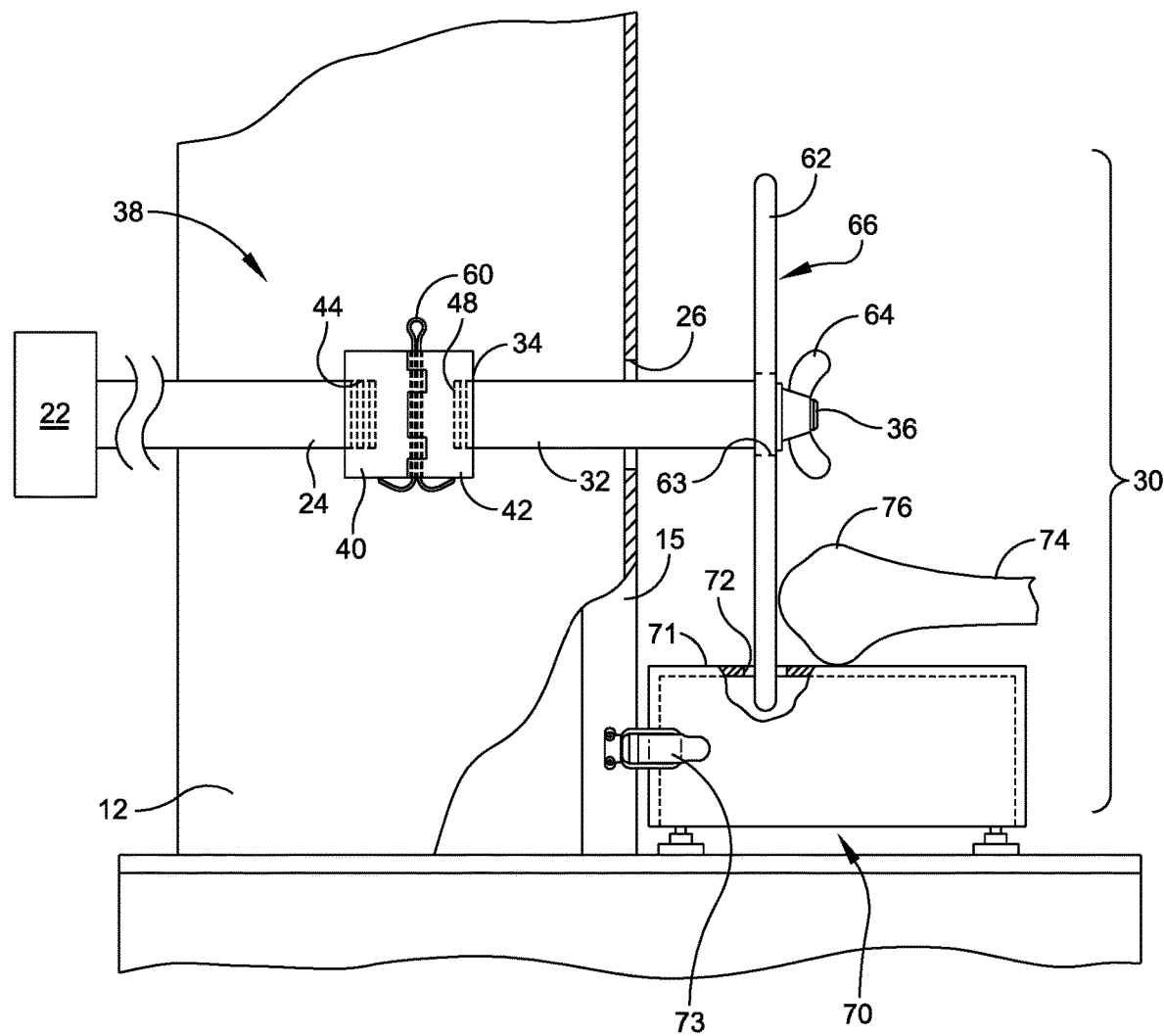
Figure 4:
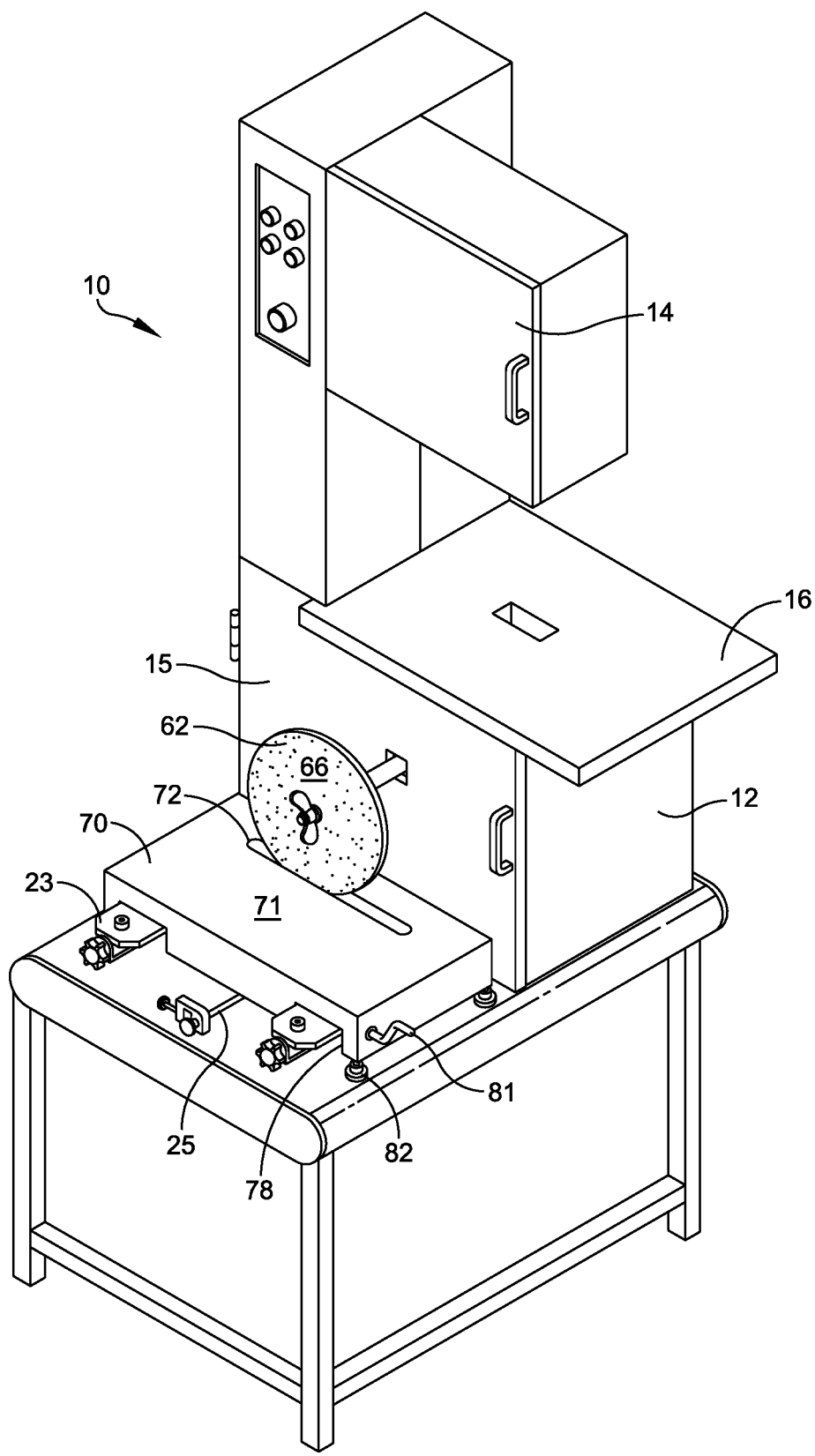
FIG. 4 illustrates a perspective view of the band saw of FIG. 1, with the osseous-sanding accessory system of FIGS. 3A-3B in the installed configuration.

FIGS. 3A-3B and 4 illustrate respective side-exploded, side, and front views of one embodiment of an osseous-sanding accessory system 30, as installed upon the first cabinet 12 of the conventional band saw 10, discussed above. In this embodiment, the osseous-sanding accessory system 30 may include a threaded drive shaft 32 having a first or power end 34 located at the primary drive shaft 24 of the band saw 10 and a second or grinding end 36 that extends outward from the first cabinet 12 through an aperture 26 formed within the first cabinet door 15. In this configuration, a power coupling 38 may operably couple the power end 34 of the threaded drive shaft 32 with the motor 22 of the band saw 10 via the band saw's primary drive shaft 24. The power coupling 38 may include one or more adaptors and/or locking pins (e.g., a cotter pin, a clevis pin) of any appropriate size, shape, type, and/or configuration installed between the primary drive shaft 24 and the power end 34 of the threaded drive shaft 32 to accomplish this operable coupling between the primary drive shaft 24 and the threaded drive shaft 32, and thus, between the band-saw motor 22 and the threaded drive shaft 32.

In one exemplary embodiment shown in FIGS. 3A-3B, the power coupling 38 may comprise a first adapter 40 and a second adapter 42. The first adapter may have a threaded female end 44 and a clevis end 46. The second adapter 42 may similarly feature a threaded female end 48 and a clevis end 50. The female ends 44, 48 of the first and the second adapters 40, 42 may threadably engage with the threaded primary drive shaft 24 and the first power end 34 of the threaded drive shaft 32, respectively. The clevis ends 46, 50 of the first and the second adapters 40, 42 may each include interlocking or mating prongs 52, 54 having respective clearance apertures 56, 58 that are adapted to receive a locking pin 60. When the interlocking prongs 52, 54 are mated, and when the locking pin 60 is inserted through the aligned clearance apertures 56, 58, as shown in FIG. 3B, the first and the second adapters 40, 42 interlock to complete the power coupling 38 between the primary drive shaft 24 of the band saw 10 and the threaded drive shaft 32 of the accessory system 30. In one embodiment, the power coupling 38 may be a standardized connector hub configured to facilitate the use of other/alternative band-saw accessories and/or attachments.

Opposite the power coupling 38, a grinding disk 62 having a center aperture 63 may be attached to the grinding end 36 of the threaded drive shaft 32 via an appropriate threaded attachment nut 64 (e.g., a standard nut or dome-shaped nut), as shown in FIG. 3A-3B, or any other appropriate fastener or attachment mechanism. The grinding disk 62 may include an outward or distal-facing abrasive surface 66. In one embodiment, the grinding disk 62 may be a 6-inch, diamond blade disk or a disk incorporating another non-particulating grit suitable for removing articular cartilage and/or cortical bone layers from donated human cadaveric femoral heads.

Figure 5:
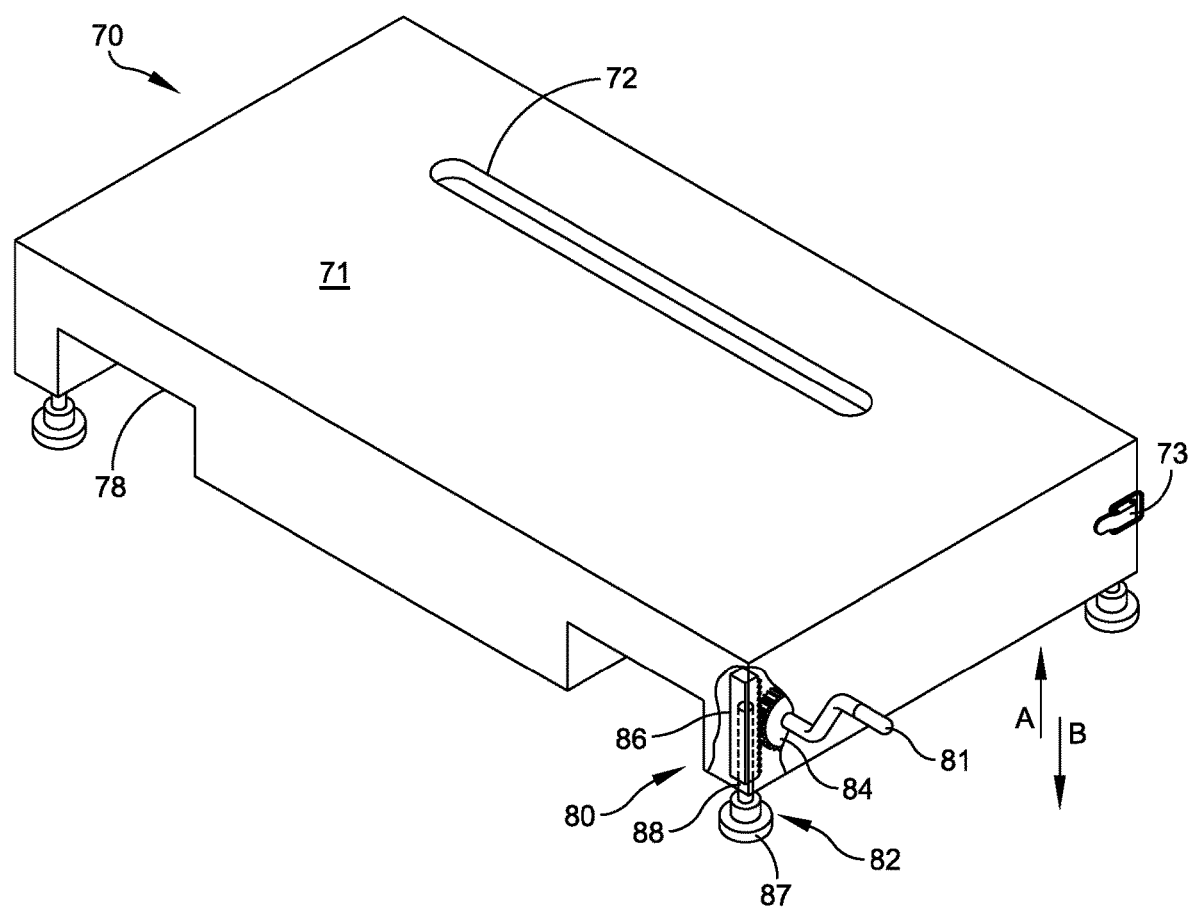
FIG. 5 illustrates a perspective view of a removable accessory table of the osseous-sanding accessory system of FIGS. 3-4.
Figure 6:
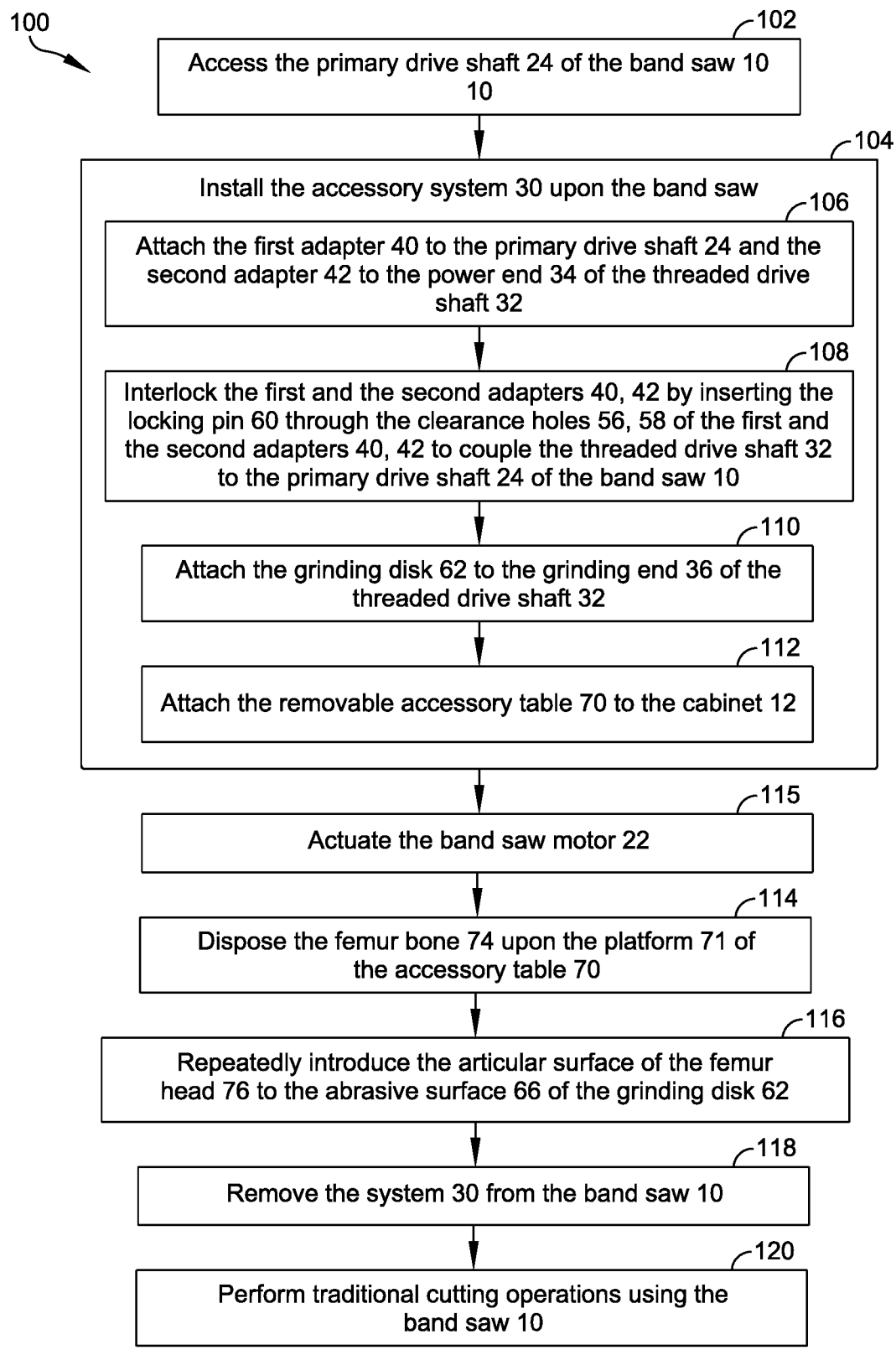
FIG. 6 provides a flowchart depicting an exemplary method of removing articular cartilage and cortical bone layers from an articular surface of a human cadaveric femur bone using a band saw fitted with the osseous-sanding accessory system of FIGS. 3-4.

Embodiments of the osseous-sanding accessory system 30 may also include one embodiment of a removable accessory table 70 shown in FIGS. 3A-3B and 4, and detailed in FIG. 5. The accessory table 70 may be attached to a base of the band saw 10 (e.g., to the lower, first cabinet 12) via one or more latches 73, clamps or other attachment mechanisms, such that the accessory table 70 is disposed directly beneath the grinding disk 62, spanning a distance to the front and to the back of the grinding disk 62.

In this embodiment, the accessory table 70 may include an upper platform 71 having a slot 72 that is sized and positioned to receive a lower portion of the grinding disk 62 when the accessory table 70 is attached. Thus, in operation, an operator may rest a femur or femur portion 74 upon the platform 71 such that a head 76 of the femur 74 contacts the abrasive surface 66 of the grinding disk 62 in a supported and stable manner that allows the operator to rely on the accessory table 70 when maneuvering the femur head 76 relative to the grinding surface 66.

Embodiments of the accessory table 70 may be configured as appropriate to accommodate the physical parameters and/or the various adjustment and/or control mechanisms (e.g., table angle adjustment, table height adjustment depth adjustment, etc.) of the band saw upon which the table 70 is installed. For example, the platform 71 of the accessory table 70 may include one or more channels 78, sized to accommodate adjustment and control mechanisms 23, 25 of the exemplary band saw 10. Alternative embodiments of the platform 71 may include any appropriate size, shape, type, and/or configuration to accommodate varying band-saw configurations.

As shown in FIG. 5, the accessory table 70 may also include a height-adjustment mechanism 80 for manually leveling and/or raising and lowering a height of the platform 71 to a level suitable for osseous-based processing operations. In one embodiment, the height-adjustment mechanism 80 may include a number of adjustable legs 82, each having a foot 87 and a body 88. Each of the legs 82 may be associated with a gear train including a toothed or geared shaft 86 that is suspended from a bottom surface of the platform 71 and disposed about the body 88 of the respective leg 82. A rotating gear 84 may be configured to engage/mesh with each of the geared shafts 86. In this embodiment, a hand crank 80 may be indirectly coupled with one of the legs 82 via the respective rotating gear 84. In operation, the operator may revolve the crank 80, which, in turn, rotates the gear 84. The gear 84 engages with the geared shaft 86 and causes the geared shaft 86, and thus the attached platform 71, to raise and lower relative to the body 88 of the leg 82 in the directions of arrows A and B, respectively. The remaining geared shafts 86 are attached to and rise with the platform 71, which, in turn, rotates the respective gears 84 and adjusts all of the legs 82 in parallel. In addition, each of the feet 87 may be threadably attached to its respective body 88, such that the feet 87 may be individually adjusted relative to the bodies 88 for leveling purposes with finer granularity.

To ensure stability and in one embodiment, the height-adjustment mechanism 80 may include a locking mechanism of any appropriate size, shape, type, and/or configuration. By way of limited example, a threaded pin or pins may engage the shaft(s) 86 at desired heights (not shown). In another embodiment, the gear train may function as a ratchet mechanism in the upward direction of arrow A, with a manual release that releases the shaft 86 and allows the shaft 86 to translate downward in the direction of arrow B.

While the exemplary height-adjustment mechanism 80 is discussed in terms of a mechanical, gear-based solution, it should be understood that the height-adjustment mechanism may be a mechanism of any appropriate type and/or configuration. For instance, the crank 80 may actuate a geared system of a different configuration or a number of hydraulic cylinders associated with each of the legs 82.

Conventional band saws have varying configurations. For example, some band saws position the motor and the primary drive shaft at the lower cabinet, while others position them in the upper cabinet. Thus, while FIGS. 3A-3B and 4 show the threaded drive shaft 32, the grinding disk 62, and the removable accessory table 70 installed upon the first (i.e., the lower) band-saw cabinet 12, it should be understood that the system 30 may be installed upon either of the band saw's pulley/cabinet arrangements 12, 14, so long as the threaded drive shaft 32 is able to operably couple with the band-saw motor 22.

The threaded drive shaft, adaptor(s), pin(s), fasteners, and removable accessory table are ideally constructed of surgical stainless steel using a minimum number of commonly available parts to facilitate easy installation/removal, use, and autoclave sterilization. Alternatively, the accessory table may be constructed of autoclavable plastics such as high-impact polyvinyl chloride (PVC), polypropylene (PP), polysulfone (PS), polyetheretherketone (PEEK), polymethylpentene (PMP), polycarbonate (PC), PTFE Resin, and polymethyl methacrylate (PMMA).

In operation, when the band saw 10 is powered, the grinding disk 62 spins (e.g., either clockwise or counter-clockwise depending on the motor configuration). The operator may place the femur bone 74 upon the platform 71 of the accessory table 70 and introduce the femoral head 76 to the abrasive surface 66 of the grinding disk 62, as shown in FIGS. 3A-3B, to efficiently and safely remove the superficial articular cartilage and cortical bone layers and expose the cancellous tissue beneath.

To demonstrate, FIG. 7 provides a flowchart depicting an exemplary method (100) of removing the superficial articular cartilage and cortical bone layers from a femoral head using a conventional band saw such as, for example, the band saw 10 outfitted with the osseous-sanding accessory system 30, discussed above. The method (100) begins with accessing the primary drive shaft 24 of the band saw 10 (102), generally by removing the associated pulley 18 from the primary drive shaft 24 to render a distal end of the shaft 24 available for an alternate use. Next, the method (100) continues with installing the osseous-sanding accessory system 30 upon the band saw 10 (104). This installation (104)

may include attaching the first adapter 40 to the primary drive shaft 24 and the second adapter 42 to the power end 34 of the threaded drive shaft 32 (106) before interlocking/mating the first and the second adapters 40, 42 by inserting the locking pin 60 through the clearance holes 56, 58 of the first and the second adapters 40, 42 to couple the threaded drive shaft 32 of the accessory system 30 to the primary drive shaft 24 of the band saw 10 (108), such that the grinding end 36 of the threaded drive shaft 32 extends outward from the first cabinet door 15 of the first cabinet 12 of the band saw 10.

Next, the installation (104) continues with attaching the grinding disk 62 to the grinding end 36 of the threaded drive shaft 32 using the attachment nut 64 (110) and attaching the removable accessory table 70 to the cabinet 12 (e.g., via one or more of the latches 73) at a height and a position at which the platform 71 is located directly beneath the grinding disk 62, and the grinding disk 62 extends into the slot 72 within the platform 71 (112).

Once the sanding accessory system is installed (104), the method (100) continues with actuating the band saw motor 22 (115), disposing the femur bone 74 upon the platform 71 of the accessory table 70 (114), and repeatedly introducing the articular surface of the femur head 76 to the abrasive surface 66 of the grinding disk 62 (116) as necessary to safely and efficiently remove the articular cartilage and the cortical bone layers from the articular surface. Once abrading operations to the femur head 76 are complete, the accessory system 30 may be removed (118) by removing the threaded drive shaft 32 and the removable accessory table 70 before the band saw 10 may once again be purposed as a conventional band saw for other processing/cutting operations (120).

The osseous-sanding accessory system 30 and associated method (100) allows for existing equipment typically housed within an osseous allograft processing environment (e.g., a tissue bank, an allograft processing center, etc.) to be multi-purposed for both traditional processing purposes and for removing the superficial tissues upon the articular surface of the human cadaveric femur head. Thus, the accessory system 30 disclosed herein enables allograft processors to avoid the expense of purchasing, operating, and maintaining separate motorized equipment for the specialized purpose of articular surface cleaning and processing within the limited space of the processing environment.

Embodiments of the osseous-sanding accessory system 30 and method (100) discussed above allow the operator to avoid the path of any conventional band-saw blade to avoid traumatic injuries and does not require the operator to employ repetitive hand or arm movements during manual tissue removal. In addition, the system requires far less training and a lower skill level than conventional removal methods and mechanisms. Moreover, the system leverages existing osseous-tissue processing equipment that is generally available in the processing environment.

Beyond superficial tissue and cortical layer removal, the system may be used to remove layers of other osseous-based materials or to shape osseous hard/solid tissues (e.g., shape cortical bone).

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. An osseous-sanding accessory system for removable installation upon a commercial band saw having a motor operably coupled with a primary drive shaft, the primary drive shaft coupled with a blade pulley housed within a cabinet, the accessory system comprising:
   a threaded drive shaft having a first end operably coupled with the motor via the primary drive shaft and a second end that extends outward from the cabinet;
   a grinding disk having an abrasive surface, a center aperture, and a lower portion disposed below the center aperture, the center aperture of the grinding disk affixed about the second end of the threaded drive shaft; and
   an accessory table having an upper platform forming a slot therein, the accessory table removably mounted to the cabinet such that the lower portion of the grinding disk extends into the slot, wherein when the motor of the band saw rotates the primary drive shaft, the threaded drive shaft rotates the grinding disk relative to the accessory table such that the abrasive surface abrades osseous tissues introduced to the abrasive surface of the grinding disk.

2. The osseous-sanding accessory system of claim 1, further comprising a power coupling between the threaded drive shaft and the primary drive shaft of the band saw, the power coupling comprising:
   a first adapter having a threaded female end and a clevis end, the threaded female end of the first adapter coupled to the primary drive shaft;
   a second adapter having a threaded female end and a clevis end, the threaded female end of the second adapter coupled to the first end of the threaded drive shaft; and
   a locking pin inserted through the clevis ends of the first and the second adapters.

3. The osseous-sanding accessory system of claim 1, wherein the grinding disk comprises a diamond blade disk.

4. The osseous-sanding accessory system of claim 1, wherein the accessory table is removably mounted to the cabinet via one or more latches.

5. The osseous-sanding accessory system of claim 1, the accessory table further comprising a height-adjustment mechanism for adjusting the upper platform to a height at which the lower portion of the grinding disk extends into the slot.

6. The osseous-sanding accessory system of claim 5, the height-adjustment mechanism comprising a manual crank extending outward from the upper platform, the manual crank indirectly coupled with a number of adjustable legs via a gear train.

7. The osseous-sanding accessory system of claim 6, the gear train comprising:
   a rotating gear coupled with the manual crank, the rotating gear meshed with a toothed shaft suspended from the platform and disposed about a body of one of the adjustable legs, wherein:
      when the manual crank is rotated in a first direction, the toothed shaft translates in an upward direction to raise the platform; and
      when the manual crank is rotated in a second direction, the toothed shaft translates in a downward direction to lower the platform.

8. An accessory assembly for adapting a band saw for use in osseous-based sanding operations, the accessory assembly comprising:
- a threaded drive shaft having a first end positioned adjacent a primary drive shaft of the band saw and a second end extending outward from a cabinet of the band saw;
- a grinding disk coupled to the second end of the threaded drive shaft; and
- a power coupling indirectly connecting a motor of the band saw with the first end of the threaded drive shaft, the power coupling comprising:
  - a first adaptor threadably coupled to the primary drive shaft of the band saw;
  - a second adaptor threadably coupled to the first end of the threaded drive shaft; and
  - a locking pin engaged with the first and the second adapters to mate the first and the second adapters with one another.

9. The accessory assembly of claim 8, wherein:
the first adapter comprises a threaded female end threadably coupled to the primary drive shaft and a pronged clevis end having at least one clearance aperture;
the second adapter comprises a threaded female end threadably coupled to the first end of the threaded drive shaft and a pronged clevis end having at least one clearance aperture; and
when the at least one clearance aperture of the pronged clevis end of the first adapter and the at least one clearance aperture of the pronged clevis end of the second adapter are aligned, the locking pin extends through the at least one clearance aperture of the first adapter and the at least one clearance aperture of the second adapter to mate the first and the second adapters with one another.

10. The accessory assembly of claim 8, further comprising a removable accessory table attached to the cabinet of the band saw directly below the grinding disk, the removable accessory table configured to support a cadaveric femur during the osseous-based sanding operations.

11. The accessory assembly of claim 10, wherein the removable accessory table comprises:
- a number of adjustable legs;
- a platform disposed above the legs, the platform having a slot configured to receive a lower portion of the grinding disk; and
- a height-adjustment mechanism associated with the number of the adjustable legs, the height-adjustment mechanism configured to raise and lower the platform to a desired height relative to the grinding disk.

12. The accessory assembly of claim 11, wherein the height-adjustment mechanism comprises a manual crank coupled with at least one of the number of the adjustable legs via a gear train.

13. The accessory assembly of claim 8, wherein the grinding disk comprises a diamond blade disk having an abrasive surface.

14. A method of removing articular cartilage and cortical bone layers from an articular surface of a human cadaveric femur bone using a band saw, the method comprising:
accessing a primary drive shaft of the band saw;
coupling a threaded drive shaft to the primary drive shaft of the band saw via a power coupling, the threaded drive shaft having a first end located at the primary drive shaft and a second end extending outward from a cabinet of the band saw;
affixing a grinding disk to the second end of the threaded drive shaft, the grinding disk having an abrasive surface;
removably attaching an accessory table to the cabinet of the band saw directly below the grinding disk, the accessory table having a number of adjustable legs that support a platform;
actuating a motor of the band saw such that the grinding disk rotates relative to the accessory table;
disposing the human cadaveric femur bone upon the platform of the accessory table; and
introducing the articular surface of the human cadaveric femur bone to the abrasive surface of the grinding disk to remove the articular cartilage and the cortical bone layers from the articular surface.

15. The method of claim 14, wherein the accessing the primary drive shaft comprises removing a blade pulley of the band saw from the primary drive shaft.

16. The method of claim 14, further comprising, after the introducing the articular surface of the human cadaveric femur bone to the abrasive surface:
removing the removable accessory table;
decoupling the power coupling to remove the threaded drive shaft; and
reinstalling the blade pulley upon the primary drive shaft to restore the band saw for use in conventional processing operations.

17. The method of claim 14, wherein the power coupling comprises a first adapter having a first threaded female end and a first clevis end with one or more first clearance apertures, a second adapter having a second threaded female end and second clevis end with one or more second clearance apertures, and a locking pin, and wherein the coupling the threaded drive shaft to the primary drive shaft of the band saw via the power coupling comprises:
threadably coupling the first threaded female end of the first adapter to the primary drive shaft;
threadably coupling the second threaded female end of the second adapter to the first end of the threaded drive shaft;
mating the first clevis end of the first adapter and the second clevis end of the second adapter; and
inserting the locking pin through the first and the second clearance apertures.

18. The method of claim 14, wherein the removably attaching the accessory table comprises latching the accessory table to the cabinet of the band saw.

19. The method of claim 18, wherein the removably attaching the accessory table further comprises adjusting a height of the platform such that a slot formed in the platform envelops a lower portion of the grinding disk.

20. The method of claim 14, wherein the grinding disk comprises a diamond blade disk.

* * * * *